United States Patent [19]

Fuchs et al.

[11] Patent Number: 5,359,062

[45] Date of Patent: Oct. 25, 1994

[54] RECOVERY OF CAPROLACTAM FROM POLYCAPROLACTAM

[75] Inventors: Hugo Fuchs, Ludwigshafen; Gerald Neubauer, Weinheim; Josef Ritz; Claus-Ulrich Priester, both of Ludwigshafen, all of Fed. Rep. of Germany

[73] Assignee: BASF Aktiengesellschaft, Ludwigshafen, Fed. Rep. of Germany

[21] Appl. No.: 54,064

[22] Filed: Apr. 29, 1993

[30] Foreign Application Priority Data

May 7, 1992 [DE] Fed. Rep. of Germany ....... 4215087

[51] Int. Cl.$^5$ .......................................... C07D 201/12
[52] U.S. Cl. .................................................. 540/540
[58] Field of Search ......................................... 540/540

[56] References Cited

U.S. PATENT DOCUMENTS 4,605,762  8/1986  Mandoki ............................. 540/540

FOREIGN PATENT DOCUMENTS

| | | | |
|---|---|---|---|
| 850614 | 9/1952 | Fed. Rep. of Germany | 540/540 |
| 851194 | 10/1952 | Fed. Rep. of Germany | 540/540 |
| 851195 | 10/1952 | Fed. Rep. of Germany | 540/540 |
| 950726 | 10/1956 | Fed. Rep. of Germany | 540/540 |
| 4811 | 8/1986 | Fed. Rep. of Germany | 540/540 |

OTHER PUBLICATIONS

*Pat. Abst. of Japan*, vol. 6, No. 94 (C-105) Jun. 2, 1982.
Derwent Publ. Ltd., week 8410, AN 78-48679A (english abstract of JP 59 006 849), (no date).
Derwent Publ. Ltd, week 7127, AN 71-46368S (english abstract of JP 46 024 388). (no date).

*Primary Examiner*—Robert T. Bond
*Attorney, Agent, or Firm*—Keil & Weinkauf

[57] ABSTRACT

Caprolactam is recovered from polycaprolactam by hydrolyric cleavage of polycaprolactam with from 5 to 50 parts by weight of water per part by weight of polycaprolactam at from 200° to 350° C. under superatmospheric pressure to give an aqueous solution or suspension which contains monomeric caprolactam and oligomers thereof and may contain polycaprolactam and subsequent isolation of monomeric caprolactam from the aqueous solution or suspension by distillation or extraction, by a process in which the hydrolyric cleavage is carried out in the presence of an alkali metal hydroxide at a pH of from 5 to 10.

7 Claims, No Drawings

RECOVERY OF CAPROLACTAM FROM POLYCAPROLACTAM

The present invention relates to a process for the recovery of caprolactam from polycaprolactam by hydrolyric cleavage of polycaprolactam with water.

In the preparation of polycaprolactam and in its processing to give moldings, such as filaments, fibers, films or injection molded or extruded articles, polycaprolactam wastes are obtained and have to be disposed of. Furthermore, the commodities produced from polycaprolactam, such as films, woven fabrics, packaging and shaped articles, finally have to be disposed of. Recovery of caprolactam from polycaprolactam is a possibility here.

U.S. Pat. No. 4,605,762 describes a process for the depolymerization of condensation polymers, such as polyesters, nylon 6,6 and polycaprolactam, by hydrolyric cleavage at from 200° to 300° C. under superatmospheric pressure and with the supply of steam. The stated U.S. patent does not describe the procedure to be adopted in order to obtain, in the hydrolyric cleavage of polycaprolactam, monomeric caprolactam which can be recycled to the purification stage in the preparation of caprolactam.

It is an object of the present invention to recover monomeric caprolactam from polycaprolactam by hydrolyric cleavage, which monomeric caprolactam has improved quality and can be recycled, without disadvantage, to the purification stage in the preparation of caprolactam.

We have found that this object is achieved by a process for the recovery of caprolactam from polycaprolactam by hydrolyric cleavage of polycaprolactam with from 5 to 50 parts by weight of water per part by weight of polycaprolactam at from 200° to 350° C. under superatmospheric pressure to give an aqueous solution or suspension which contains monomeric caprolactam, oligomers thereof and polycaprolactam and subsequent isolation of monomeric caprolactam from the aqueous suspension by distillation or extraction, wherein the hydrolyric cleavage is carried out with the addition of an alkali metal hydroxide at a pH of from 5 to 10.

The novel process has the advantages that it gives caprolactam of improved quality, which permits the monomeric caprolactamthus obtained to be recycled to the purification stage in the preparation of caprolactam, and that it takes place with a higher yield and a small amount of unutilizable residues remains.

According to the invention, the starting material used is polycaprolactam which is to be disposed of or wastes obtained in the preparation of polycaprolactam and its processing to give filaments, films or injection molded or extruded articles, or shaped commodities, such as films, packaging, woven fabrics, filaments or extruded articles, which are to be disposed of. Advantageously, the polyamide articles to be cleaved are comminuted prior to the hydrolyric cleavage, for example by milling, if necessary after prior compaction. Polycaprolactam having a particle size of from 1 to 100 mm is advantageously used.

For the hydrolytic cleavage, from 5 to 50, in particular from 10 to 20, parts by weight of water are used per part by weight of polycaprolactam. The reaction is carried out at from 200° to 350° C., advantageously from 210° to 300° C. The hydrolyric cleavage is furthermore effected under superatmospheric pressure, for example at from 20 to 200, in particular from 20 to 100, bar. It has proven useful to increase the pressure by forcing in an inert gas, such as nitrogen. Of course, the pressure and temperature conditions must be matched with one another so that a liquid phase is present.

As a rule, residence tithes of from 3 to 6 hours are maintained in the hydrolytic cleavage. It has proven suitable for at least 60, in particular from 60 to 90, % by weight of the polycaprolactam used to be cleaved into caprolactam.

An essential feature of the invention is that the hydrolyric cleavage is carried out in the presence of an alkali metal hydroxide, such as potassium hydroxide or, in particular, sodium hydroxide, at a pH of up to 10, preferably from 6 to 8.

After the pressure has been let down, an aqueous solution or suspension which contains monomeric caprolactam and oligomers thereof and may contain unhydrolyzed polycaprolactam is obtained. Monomeric caprolactam is obtained from this aqueous solution or suspension by distillation or is separated off by extraction with a water-soluble salt, for example benzene, toluene or xylene, caprolactam being readily obtainable from such an extract by distilling off the solvent.

In a particularly preferred procedure, the conversion of at least 60% is maintained in the cleavage of polycaprolactam, caprolactam is extracted from the resulting aqueous solution or suspension with a water-insoluble organic solvent and the remaining aqueous solution or suspension, which contains oligomers of caprolactam and may contain uncleaved polycaprolactam, is recycled to the hydrolytic cleavage.

The caprolactamthus obtainable is advantageously fed to the purification stage in the preparation of caprolactam.

The Examples which follow illustrate the process according to the invention.

EXAMPLE 1

1,000 ml of water and 100 g of nylon 6 were introduced into a 2 liter autoclave. 0.5 g of sodium hydroxide were added. The autoclave was flushed with nitrogen and nitrogen was forced in to a pressure of 5 bar. Thereafter, the temperature was increased to 250° C. while stirring. The operating pressure was about 50 bar. After 5 hours, the autoclave was cooled to room temperature. A virtually colorless clear solution was obtained.

After extraction with toluene, the solvent was removed by distillation from the organic phase. 67 g of residue were obtained, from which 65 g of pure caprolactam were recovered by distillation at 105° C. and 4 mbar.

30 g of unconverted polymide remained in the extracted aqueous phase.

The lactam had the following quality characteristics:

| | |
|---|---|
| Permanganate titration number (PTN) | 52 |
| Extinction of a 50% strength aqueous solution at 290 nm, 1 cm cell length | 0.19 |
| Volatile bases meq/kg | 0.29 |
| Free acids meq/kg | 0.08 |
| pH of a 25% strength solution | 6.5 |
| Impurities determined by GC, in ppm | 214 |
| Permanganate titration number (PTN) | |

The number indicates the consumption of 0.1N (0.02 mol/l) potassium permanganate solution in ml per kg of caprolactam. Titration is carried out dropwise at 20° C. in 50% strength by weight sulfuric acid until a slight pink coloration develops which remains for at least 1 minute.

COMPARATIVE EXAMPLE

The experiment was repeated as described in Example 1. However, no sodium hydroxide solution was added to the autoclave batch.

Working up was carried out, also as described, by toluene extraction followed by distillation.

| | |
|---|---|
| PTN | 126 |
| Extinction of a 50% strength aqueous solution at 290 nm, 1 cm cell length | 0.11 |
| Volatile bases meq/kg | 0.31 |
| Free acids meq/kg | 11.2 |
| pH | 4.8 |
| Impurities determined by GC, in ppm | 381 |

EXAMPLE 2

30 g of uncleaved extraction residue or aminocaproic acid product from Example 1 were then cleaved in an autoclave under the conditions of Example 1, 0.5 g of sodium hydroxide was added and nitrogen was forced in to a pressure of 5 bar. After a residence time of 5 hours at 250° C. and 50 bar, the aqueous solution was extracted and the extract was worked up. 20.5 g of caprolactam having the following characteristics were obtained:

| | |
|---|---|
| PTN | 65 |
| Extinction of a 50% strength aqueous solution at 290 nm, 1 cm cell length | 0.50 |
| Volatile bases meq/kg | 0.80 |
| Free acids meq/kg | 0.1 |

-continued

| | |
|---|---|
| pH | 6.2 |
| Impurities determined by GC, in ppm | 300 |

We claim:

1. A process for the recovery of caprolactam from polycaprolactam by hydrolyric cleavage of polycaprolactam with from 5 to 50 parts by weight of water per part by weight of polycaprolactam at from 200° to 350° C. under superatmospheric pressure to give an aqueous solution or suspension which contains monomeric caprolactam and oligomers thereof and may contain polycaprolactam and subsequent isolation of monomeric caprolactam from the aqueous solution or suspension by distillation or extraction, wherein the hydrolytic cleavage is carried out in the presence of an alkali metal hydroxide.

2. A process as claimed in claim 1, wherein a temperature of from 210° to 300° C. is maintained.

3. A process as claimed in claim 1, wherein a pressure of from 20 to 100 bar is maintained.

4. A process as claimed in claim 1, wherein sodium hydroxide is present.

5. A process as claimed in claim 1, wherein a residence time of from 3 to 6 hours is maintained in the hydrolyric cleavage.

6. A process as claimed in claim 1, wherein from 10 to 20 parts by weight of water are used per part by weight of polycaprolactam.

7. A process as claimed in claim 1, wherein a conversion of at least 60% is maintained in the hydrolyric cleavage of polycaprolactam, caprolactam is extracted from the resulting aqueous solution or suspension with a water-insoluble organic solvent and the remaining aqueous solution or suspension, which contains oligomers of caprolactam and may contain uncleaved polycaprolactam, is recycled to the hydrolyric cleavage.

* * * * *

UNITED STATES PATENT AND TRADEMARK OFFICE
CERTIFICATE OF CORRECTION

PATENT NO. : 5,359,062

DATED : October 25, 1994

INVENTOR(S) : Fuchs et al

It is certified that error appears in the above-indentified patent and that said Letters Patent is hereby corrected as shown below:

IN THE ABSTRACT

Line 2: "hydrolyric" should read -- hydrolytic --

Line 10: "hydrolyric" should read -- hydrolytic --

IN THE CLAIMS

Claim 1, column 4, line 8:
"hydrolyric" should read -- hydrolytic --

UNITED STATES PATENT AND TRADEMARK OFFICE
CERTIFICATE OF CORRECTION

PATENT NO. : 5,359,062
DATED : October 25, 1994
INVENTOR(S) : Fuchs et al

It is certified that error appears in the above-indentified patent and that said Letters Patent is hereby corrected as shown below:

Claim 5, column 4, line 27:
   "hydrolyric" should read -- hydrolytic --

Claim 7, column 4, line 32:
   "hydrolyric" should read -- hydrolytic --

Claim 7, column 4, line 38:
   "hydrolyric" should read -- hydrolytic --

Signed and Sealed this

Twentieth Day of December, 1994

*Attest:*

BRUCE LEHMAN

*Attesting Officer*  *Commissioner of Patents and Trademarks*